United States Patent [19]

Compton et al.

[11] Patent Number: 4,725,406
[45] Date of Patent: Feb. 16, 1988

[54] APPARATUS AND METHOD FOR DIAGNOSTIC ANALYSIS OF BIOLOGICAL FLUIDS

[75] Inventors: Scott W. Compton, Vallejo, Calif.; James E. Stanchfield, Rockville, Md.

[73] Assignee: American Bionetics, Inc., Hayward, Calif.

[21] Appl. No.: 789,325

[22] Filed: Oct. 21, 1985

[51] Int. Cl.⁴ .................. G01N 1/48; G01N 21/06; C12M 1/40
[52] U.S. Cl. ........................... 422/58; 422/104; 422/86; 252/408.1; 435/288; 435/805; 435/287
[58] Field of Search ............ 422/58, 59, 60, 104, 422/69, 99, 86, 88; 435/288, 296, 805, 287; 252/408.1

[56] References Cited

U.S. PATENT DOCUMENTS

| 2,371,405 | 3/1945 | Munn | 422/59 |
|---|---|---|---|
| 3,033,655 | 5/1962 | Grosskopf | 422/88 X |
| 3,884,641 | 5/1975 | Kraffczyk et al. | 422/58 X |
| 4,090,850 | 5/1978 | Chen et al. | 422/58 X |
| 4,159,193 | 6/1979 | Gauntley et al. | 422/58 X |
| 4,235,097 | 11/1980 | Krina et al. | 422/88 X |
| 4,277,251 | 7/1981 | Leichnitz | 422/59 X |
| 4,585,623 | 4/1986 | Chandler | 422/58 X |

FOREIGN PATENT DOCUMENTS 0119858 9/1984 European Pat. Off. .
83/01308 4/1983 PCT Int'l Appl. .

Primary Examiner—John F. Terapane
Assistant Examiner—Susan Wolffe
Attorney, Agent, or Firm—Julian Caplan

[57] ABSTRACT

Apparatus for immunoassay of biological fluids, e.g. for AIDS antibodies, comprising an enclosed channel with fittings at the ends and a transparent top, together with a strip of nitrocellulose paper or other suitable material impregnated with antigens to the antibodies which are to be defected. The apparatus may have a single channel or it may have multiple channels.

2 Claims, 8 Drawing Figures

APPARATUS AND METHOD FOR DIAGNOSTIC ANALYSIS OF BIOLOGICAL FLUIDS

This invention relates to apparatus and to a method for diagnostic analysis of biological fluids. The invention has wider application but will be described with particular reference to diagnosing human blood sera for the presence of antibodies indicative of the virus causing acquired immune deficiency syndrome (AIDS).

A currently widely used procedure for detecting AIDS antibodies is the procedure known as the Western technique. In this technique, antigens derived from the AIDS virus, HTLV-III, are prepared by suitable treatment of the virus. These antigens are derived from the protein component of the virus and are a mixture of proteins, or oligopeptides, resulting from denaturing the protein component of the virus. These oligopeptides include the components (the antigens) which give rise to antibodies produced by the human host affected by the virus. This antigen mixture is available from the National Cancer Institute, National Institutes of Health Biological Modifier Program, Washington, D.C. and from several U.S. commercial sources.

This antigen mixture is separated into its components by electrophoresis, e.g. in a polyacrylamide gel. The antigens in the gel are transferred to a paper strip, e.g., nitrocellulose paper, and are immobilized on the paper. This paper is then treated by an immunoassay method with the serum to be diagnosed, e.g., serum from blood samples intended for a blood bank or serum from a person suspected of having, or of having had AIDS.

The procedure thus briefly described is widely known and is described in, for example, Tsang, V.C.W. et al. "Enzyme-Linked Immunoelectrotransfer for Blot Technique (EITB) (Western Blot) for HTLV-III/LAV Antibodies." Developmental Procedure. U.S. Department of Health and Human Services, Public Health Service. Center for Disease Control. Atlanta, GA. March, 1985.

A need exists for a device to hold these paper strips and to carry out the immunoassay method, such device being simple, easy to use and requiring minimal quantities of fluids and reagents. Also the device should be relatively safe to use.

Certain equipment is available, e.g., that of Mast Medical Industries, Ltd., of Menlo Park, Calif., such as described in European patent application 0119058 and International patent application No. WO 83/01308. However such devices are disadvantageous for one or more of the following reasons: The requirement that impregnated threads be used to immobilize antigens, which is time consuming and expensive; a requirement that radioactively labeled materials or chemicals for chemiluminescent detection be used, which is potentially hazardous and/or is expensive; a requirement for expensive ancillary equipment for visualization and documentation of results; expensive sonic welding procedures in forming the apparatus resulting in permanently sealed, non-reuseable apparatus; and the use of non-standard male type connections on the outlet side which precludes or makes difficult the use of standard low fluid handling accessories.

It is an object of the present invention to provide devices and a method for carrying out such immunoassays which obviate one or more of the disadvantages noted above.

Certain embodiments of the invention are illustrated by way of example in the accompanying drawings, in which FIG. 1 is a view of the top of a nitrocellulose strip which is employed to carry the antigens and which is inserted in the apparatus illustrated in FIGS. 2, 3, 4 and 5;

Figure 1:
Figure 2:
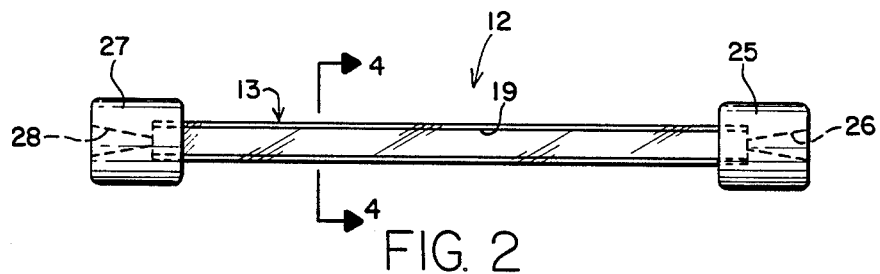
FIG. 2 is a side view of the device of the invention.
Figure 3:
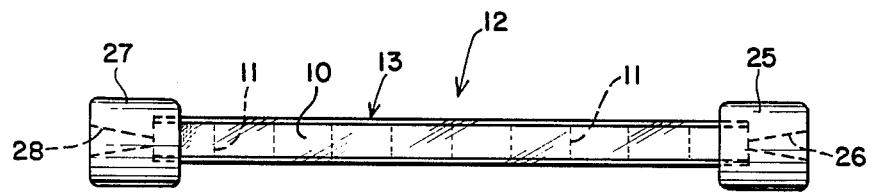
FIG. 3 is a top view thereof.
Figure 4:
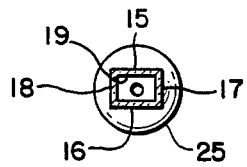
FIG. 4 is a section taken along the line 4—4 of FIG. 2.
Figure 5:
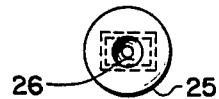
FIG. 5 is an end view as seen from either end of the device.

Referring now to FIG. 1, a paper strip generally designated as 10 is there shown, such being preferably a nitrocellulose strip, although other materials capable of performing the same functions may be used. Typical dimensions are a length of 10 centimeters and a width of 5 millimeters. Broken lines, indicated by the reference numeral 11, illustrate the positions of antigens intended to react with antibodies of the fluid under investigation. This strip is prepared by the procedure described above, that is to say, by treating the viral agent, e.g., the AIDS virus, to separate the protein component from the DNA component, then subjecting the resulting mixture of antigens to separation by electrophoresis and transferring the separated antigens to the paper strip.

Referring now to FIGS. 2, 3, 4 and 5, the apparatus is generally designated by the reference numeral 12 and it comprises an enclosed body portion 13 which has top and bottom portions 15 and 16 and side portions 17 and 18. The body 13 may be of any suitable, clear plastic material, e.g. polystyrene or it may be of opaque or non-plastic material provided the top 15 is transparent. As will be seen, the body portion 13 provides an elongated chamber 19 of rectangular shape. Such a section is preferred but other configurations may be employed. The body portion is open at its ends and is provided with an end fitting 25 having an opening 26 and another end fitting 27 having an opening 28. These end fittings are preferably of elastomeric material and although both are shown as being female type connections, one of them may be a female and the other a male type connection or both may be male type connections. The fittings 25 and 27 are preferably of a type which will fit standard luer fluid handling accessories.

In use, a paper strip as shown at 10 in FIG. 1 is inserted in the body portion of the apparatus and the end fittings 25 and 27 are applied. Then, assuming dimensions such as described above, a 5 ml portion of a buffer solution A is flushed through the chamber to wet the paper strip. This can be conveniently done by fitting a two-way stop cock and syringe to one of the fittings, assumed to be fitting 25 for purposes of description, and a pipette tip is fitted to the fitting 27 at the other end. The buffer solution is, for example, a phosphate buffered saline solution containing Tween brand non-ionic detergent. The buffer solution is drawn into the device by inserting the pipette into a body of the buffer and using the syringe to draw the buffer solution into the chamber 19. Then the chamber is allowed to drain excess buffer. Then the fluid under investigation, e.g., 1.0 ml of human serum being analyzed for the presence of AIDS antibodies, suitably diluted 100:1 with the same buffer solution, is drawn into the chamber 19 by the same procedure after which the syringe and pipette are removed, the ends of the device are plugged, and the serum is allowed to incubate at 37° C. for one hour. Then the serum is drained from the chamber 19 and it is flushed with the same buffer solution. Then it is filled with horseradish peroxidase conjugated anti-human IgG and is incubated for thirty minutes at room temperature. The chamber 19 is again flushed with 25 to 50 mls of the same buffer solution and is filled with an enzyme substrate solution of 3,3 diaminobenzidine and incubated 5 to 10 minutes at room temperature. The apparatus is then allowed to drain and it is flushed with 20 mls of de-ionized water. The paper strip 10 is then observed. Colored bands in positions corresponding to the relevant antigens will indicate the presence of antibodies in the fluid.

The quantities indicated are suitable for apparatus of typical dimensions of 10 cm in length and a chamber 19 having a cross section of 0.20 square centimeter providing a volume of 2 cubic centimeters. This is quite adequate for use and conserves reagents. Also the procedure minimizes exposure of the person using the apparatus.

Figure 6:
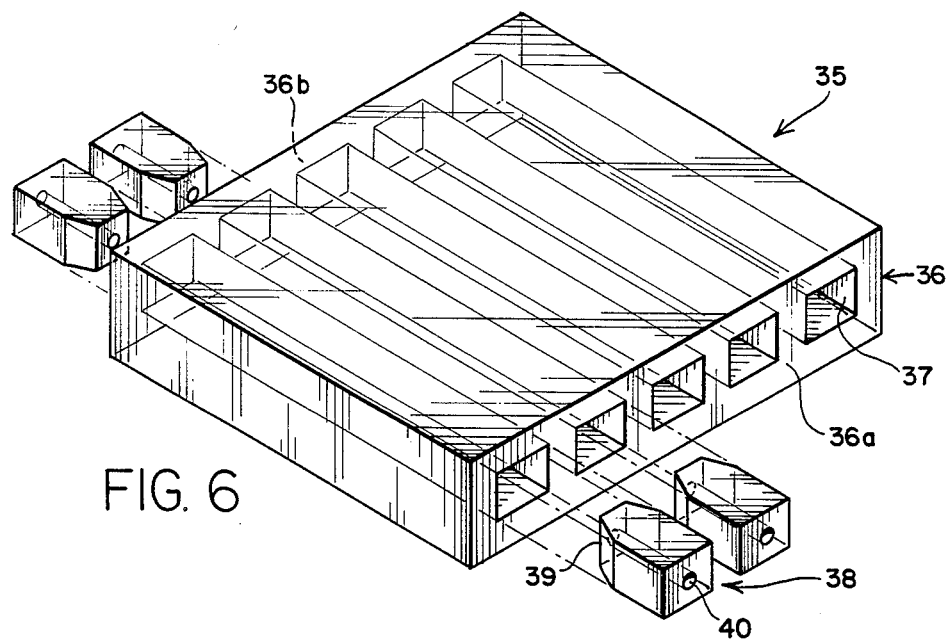
FIG. 6 is a perspective view of a multiple channel device.

Referring now to FIG. 6, a multiple channel device is shown and is generally designated by the reference numeral 35. Preferably it is made of a single block 36 of transparent plastic material, e.g. polystyrene. This block is provided with a suitable number of parallel channels 37 extending through the block from face 36a to face 36b. These channels are preferably rectangular in cross section. They may be formed by drilling or by casting and in the latter case the device may be cast in two sections, an upper section and a lower section, which are then cemented together.

At each end of each channel there is a cap 38 tapered at one end at 39 to fit snugly into an open end of a channel 37. Each cap is provided with a passage 40 extending through the cap which can fit standard fluid handling equipment.

In use a paper strip such as shown at 10 in FIG. 1 is inserted in each channel and is used in the manner described above. Suitable manifolding equipment (not shown) may be used to carry out multiple assays in the manner described above.

Figure 7:
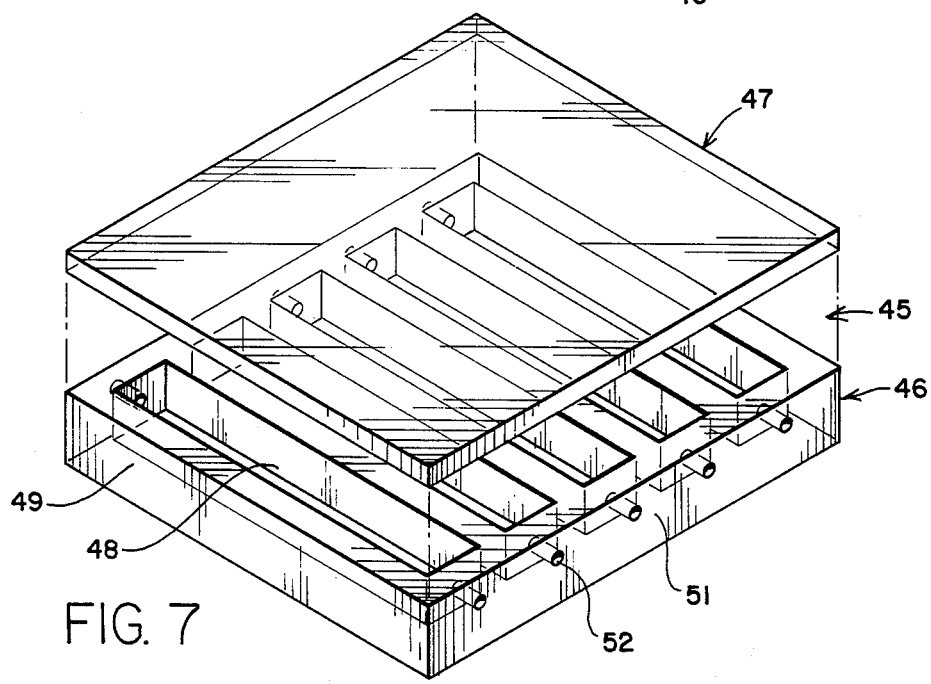
FIG. 7 is a perspective view of an alternative multiple channel device.
Figure 8:
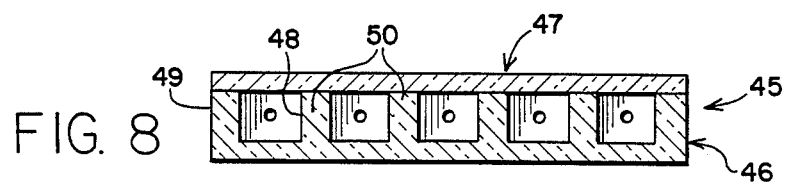
FIG. 8 is a section along the line 8—8 of FIG. 7.

Referring now to FIGS. 7 and 8, another form of multiple channel device 45 is shown having a body portion 46 and a cover portion 47. The body 46 is preferably transparent plastic and the top 47 is transparent, preferably plastic. The plastic may be, for example, polystyrene.

The body 46 is formed with channels 48 formed and separated by the sides 49 and the spacers 50. The channels 51 are provided with openings 52 into which fittings (not shown) may be inserted.

The cover 47 is secured to the body 46, e.g. by clamps (not shown) after paper strips 10 are inserted in the channels. The device is used as described above with reference to FIGS. 1 to 6.

In the device of FIG. 6, the channels 37 may be fitted with paper strips 10 and the caps 38 may be permanently attached for a one time use, or the caps may be removable for reuse.

In the device of FIGS. 7 and 8, the cover 47 may be permanently secured to the body 46 after placing paper strips in the channels 48, for a one time use, or the cover may be removable for re-use.

Although the invention has been described with particular reference to analysis for AIDS antibodies it is generally useful for other purposes, e.g., for determining antibodies to hepatitis, to herpes simplex and to other fluids whose major antigens have been identified.

What is claimed is:

1. A multiple chamber assay device comprising
    a plurality of flat, narrow, elongated paper strips each separately impregnated at intervals with antigens selected to be reactive with antibodies,
    a casing formed with a corresponding plurality of rectangular cross-section chambers,
    each said chamber having a flat bottom dimensioned to receive one said strip extending flat longitudinally of said chamber and sides and a top,
    said casing being transparent so that changes in said strips may be observed through said casing,
    each said chamber having opposed open rectangular ends dimensioned and shaped to receive insertion of one said paper strip,
    removable closures at each end of each chamber,
    each said closure comprising an apertured cap fitting into an end,
    and means in each said closure co-operative with an external source to inject fluid into said chamber and discharge fluid from said chamber.

2. The assay device according to claim 1 in which the top is fixed and not removable.

* * * * *